(12) United States Patent
Morinaga (10) Patent No.: US 6,266,137 B1
(45) Date of Patent: Jul. 24, 2001

(54) PARTICLE DETECTING APPARATUS USING TWO LIGHT BEAMS

(75) Inventor: Shirou Morinaga, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/281,285

(22) Filed: Mar. 30, 1999

(30) Foreign Application Priority Data

Apr. 10, 1998 (JP) .................................................. 10-099018

(51) Int. Cl.[7] .................................................. G01N 21/00
(52) U.S. Cl. .................................... 356/237.1; 356/237.4; 356/338
(58) Field of Search .............................. 356/237.1, 237.2, 356/237.3, 237.4, 237.5, 237.6, 239.1, 239.3, 239.7, 394, 319, 328, 326, 338; 250/559.41; 385/12

(56) References Cited

U.S. PATENT DOCUMENTS

| 5,179,422 | * | 1/1993 | Peterson | 356/239 |
| 5,486,919 | * | 1/1996 | Tsuji et al. | 356/349 |
| 5,917,590 | * | 6/1999 | Greve | 356/237.3 |
| 5,936,726 |   | 8/1999 | Takeda et al. | 356/237.2 |
| 6,157,444 | * | 12/2000 | Tomita et al. | 356/237.1 |

FOREIGN PATENT DOCUMENTS

| 55-20406 | 2/1980 | (JP) . |
| 2-61540 | 3/1990 | (JP) . |
| 6-148085 | 5/1994 | (JP) . |
| 7-294422 | 11/1995 | (JP) . |
| 382738 | 2/2000 | (TW) . |

OTHER PUBLICATIONS

Japanse Office Action dated Nov. 17, 2000, with partial English translation.
English translation of Taiwanese Office Action dated Dec. 21, 2000.
Japanese Office Action dated Aug. 22, 2000, with partial translation.

* cited by examiner

Primary Examiner—Hoa Q. Pham
(74) Attorney, Agent, or Firm—McGinn & Gibb, PLLC

(57) ABSTRACT

A particle detecting apparatus for testing a substrate with a film on its surface includes a light source section, an optical system, a light quantity measuring section and an operation section. The light source section emits first and second light beams respectively having first and second wavelengths which are different from each other. The optical system directs the first and second light beams to an incident point on the substrate, wherein the first and second light beams are scattered on the substrate to produce first and second scattered light beams. The light quantity measuring section measures a quantity of the first scattered light beam and a quantity of the second scattered light beam. The operation section detects a foreign particle on or in the film based on the first scattered light beam quantity and the second scattered light beam quantity measured by the light quantity measuring section.

23 Claims, 4 Drawing Sheets

PARTICLE DETECTING APPARATUS USING TWO LIGHT BEAMS

BACKGROUND OF THE INVENTION

1. Field of the Invention

The present invention relates to a particle detecting apparatus for a substrate with a film on its surface, and more particularly a particle detecting apparatus which can distinguish and detect a foreign substance on or in the film.

2. Description of the Related Art

With high integration of a semiconductor device, formation of a fine wiring pattern and fine gate pattern is requested. When there is a foreign substance on the pattern, a short circuit is sometimes formed due to the foreign substance. Also, the flatness of an interlayer insulating film is sometimes degraded by the foreign substance so that an upper wiring pattern is broken. With the high integration of the semiconductor device, even if the foreign substance has a small diameter, the foreign substance influences severely on the break of the wiring pattern.

In order to prevent such an influence, a particle detecting method is requested which can detect a particle with a smaller size. The particle with the smaller size could be detected by use of a laser beam with a shorter wavelength. For example, a particle with the size of 0.1 $\mu$M can be detected by an Ar laser beam. However, when there is a film of a material such as $SiO_2$ and SiN formed on a Si substrate, a scattered light beam by the foreign substance is hidden in a scattered light beam by the film, because the laser beam is reflected, absorbed or refracted. As a result, the scattered light beam by the film functions as noise so that it is difficult to detect the foreign substance in a high precision.

It is supposed that the maximum voltage corresponding to a quantity of scattered light beam by the foreign substance is represented by V1 and the maximum voltage of the noise is represented by V2. In this case, the foreign substance cannot be distinguished from the noise, if V1/V2 is not larger than 1 at least. This value is desirably equal to or more than 3. Therefore, the laser wavelength should be changed in accordance with the film thickness and the material of the film. However, it is impossible to cope with problems such as different light absorption and reflectivity depending on the film thickness and the film material only by changing the laser wavelength.

When the wavelength is made short, the light beam quantity transmitting a silicon film formed on a wafer surface sometimes decreases remarkably, so that the existence of a foreign substance particle in the silicon film cannot be detected. A laser unit with at least 2 wavelengths must be used to detect the existence of the foreign substance particle with a small size from the scattered light beam which is influenced by 2 variables of the film thickness and the particle diameter.

A method of detecting a particle by use of such a laser unit with 2 wavelengths is described in Japanese Laid Open Patent Application (JP-A-Heisei 6-148085). In this method, the degradation of the detection precision of a foreign substance particle in the wafer surface due to the interference depending upon the change of the film thickness can be prevented. That is, the method can obtain information relating to the change of the film thickness, but can not obtain information in the direction of the depth in the film. The information which is more important than the film thickness change is existence or non-existence of a foreign substance particle in the film, e.g., a hole in the film. Because the intensity of a light beam scattered by the hole is local but large, it is a detection object which is more important than the film thickness change. When the light beam is scattered by the hole, the film thickness information is not substantively gotten. A method of detecting the existence or non-existence of a foreign substance particle in the substrate surface can be surely is demanded even if the film thickness information is not obtained.

SUMMARY OF THE INVENTION

An object of the present invention is to provide a particle detecting apparatus which can obtain information of a foreign substance particle in a film to reliably detect the foreign substance particle in a substrate surface.

Another object of the present invention is to provide a particle detecting apparatus which can reliably detect a foreign substance particle in a substrate surface by removing information in the direction of the thickness of the substrate.

Still another object of the present invention is to provide a particle detecting apparatus which can reliably detect a foreign substance particle in a film and a foreign substance particle on a film surface.

Yet still another object of the present invention is to provide a particle detecting apparatus which can obtain information of a foreign substance particle in a film formed on a substrate to detect the foreign substance particle with the size equal to or less than 0.1 $\mu$m on a film surface.

In order to achieve an aspect of the present invention, a particle detecting apparatus for testing a substrate with a film on its surface includes a light source section, an optical system, a light quantity measuring section and an operation section. The light source section emits first and second light beams respectively having first and second wavelengths which are different from each other. The optical system directs the first and second light beams to an incident point on the substrate, wherein the first and second light beams are scattered on the substrate to produce first and second scattered light beams. The light quantity measuring section measures a quantity of the first scattered light beam and a quantity of the second scattered light beam. The operation section detects a foreign particle on or in the film based on the first scattered light beam quantity and the second scattered light beam quantity measured by the light quantity measuring section.

The first and second light beams may be directed to the substrate at a same time. In this case, the light quantity measuring section includes a beam collecting section for collecting the first scattered light beam and the second scattered light beam, a light wave guide for guiding the first scattered light beam and the second scattered light beam, a spectroscope for separating the first scattered light beam and the second scattered light beam guided by the light wave guide, a first measuring section for measuring the quantity of the first scattered light beam separated by the spectroscope, and a second measuring section for measuring the quantity of the second scattered light beam separated by the spectroscope. The beam collecting section may include a set of optical fibers, wherein an end of each of the optical fibers is arranged on a semi-spherical surface having the incident point as a center and the other end is connected to the light wave guide. Also, the beam collecting section and the light wave guide are made as a unit, and the light wave guide includes the set of optical fibers. Instead, the beam collecting section may include a set of optical fibers and a set of lenses, each of which is provided for one of the optical fibers in front of the end. An end of each of the optical fibers is provided on a semi-spherical surface having the incident point as a center and the other end is connected to the light wave guide.

The first and second light beams may be alternatively directed to the substrate. In this case, it is desirable that the light quantity measuring section includes a beam collecting section for collecting the first scattered light beam and the second scattered light beam, a light wave guide for guiding the first scattered light beam and the second scattered light beam, and a measuring section for measuring the quantity of the first scattered light beam and the quantity of the second scattered light beam by the light wave guide. Also, the beam collecting section may include a set of optical fibers. An end of each of the optical fibers is arranged on a semi-spherical surface having the incident point as a center and the other end is connected to the light wave guide. Instead, the beam collecting section may include a set of optical fibers and a set of lenses, each of which is provided for one of the optical fibers in front of the end. An end of each of the optical fibers is provided on a semi-spherical surface having the incident point as a center and the other end is connected to the light wave guide.

It is preferable that the wavelength of the first light beam is smaller than a grain diameter of the foreign particle. Especially, the wavelength of the first light beam is preferably shorter than 488 nm.

The wavelength of the first light beam may be smaller than that of the second light beam, and the wavelength of the second light beam may be smaller than a grain diameter of the foreign particle.

In order to achieve another aspect of the present invention, a method of detecting a foreign particle on or in a film formed on a substrate, includes:

emitting a first light beam a first wavelength;

emitting a second light beam having a second wavelength which is different from the first wavelength;

directing the first and second light beams to an incident point on the substrate;

scattering the first and second light beams by the substrate with the film;

measuring a quantity of the first scattered light beam and a quantity of the second scattered light beam; and detecting a foreign particle on or in the film based on the first scattered light beam quantity and the second scattered light beam quantity measured by the light quantity measuring section.

DESCRIPTION OF THE PREFERRED EMBODIMENTS

A particle detecting apparatus of the present invention will be described below with reference to the attached drawings.

Figure 1:
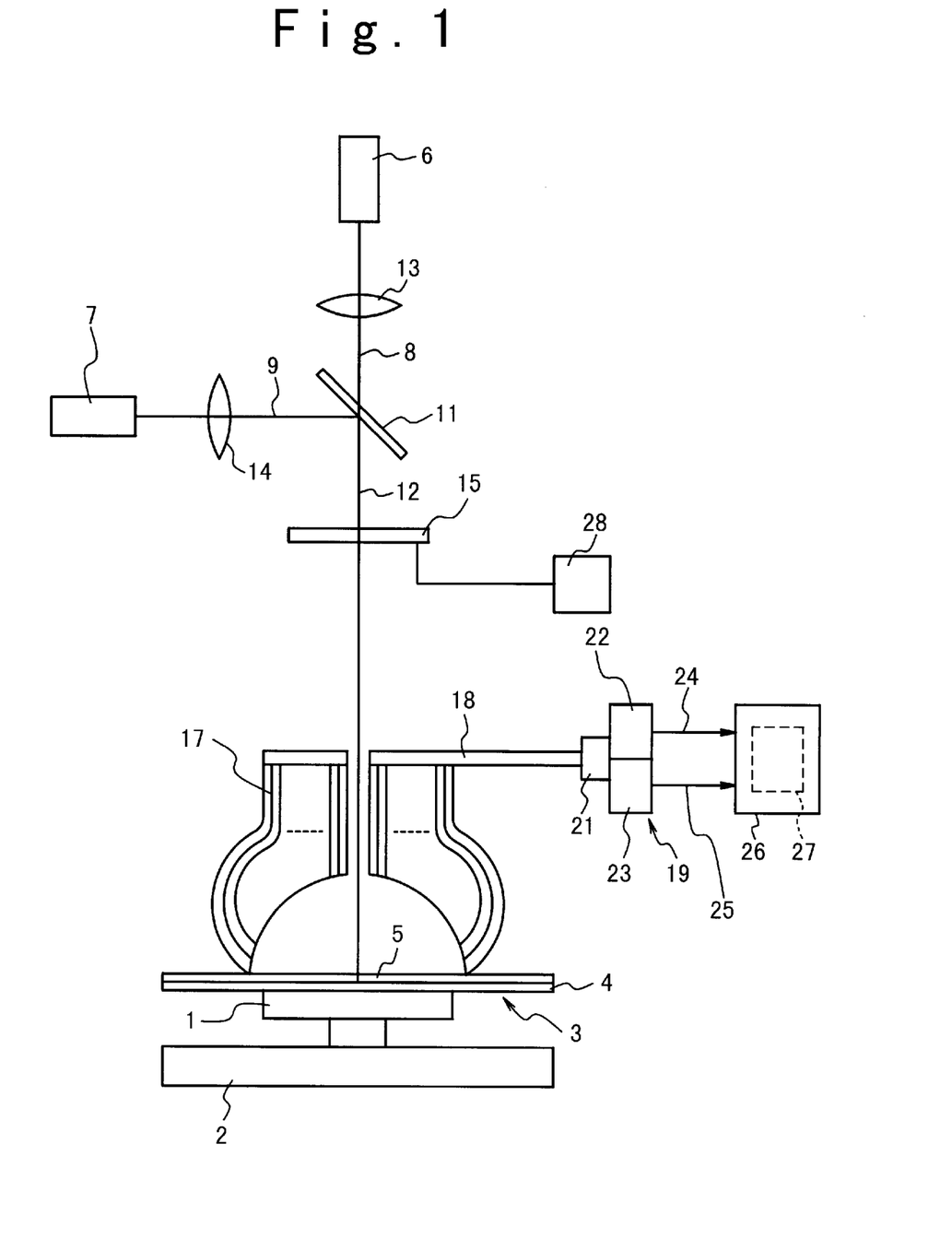
FIG. 1 is a block diagram of an optical system of a particle detecting apparatus according to a first embodiment of the present invention.

FIG. 1 is a block diagram showing the particle detecting apparatus according to the first embodiment of the present invention. Referring to FIG. 1, a movement body 1 can be moved to an optional position on the two-dimensional plane by an X-Y drive mechanism 2. A substrate 3 for a semiconductor circuit device is fixed and supported on the movement body 1. The substrate 3 for the semiconductor circuit structure is formed from a semiconductor substrate 4 and a silicon film 5 formed on the semiconductor substrate 4. The silicon film 5 is formed of material such as silicon oxide and silicon nitride.

A laser source is composed of a short wavelength laser source 6 and a long wave length laser source 7. The wavelength of the laser beam emitted from the short wavelength laser source 6 is shorter than that of the laser beam emitted from the long wave length laser source 7. The wavelength of 337 nm, 488 nm, 532 nm, or 810 nm are known as the wavelength of the used laser beam source. First laser beam 8 and second laser beam 9 are emitted from the short wavelength laser source 6 and the long wave length laser source 7 through lenses 13 and 14, respectively, and are synthesized into a synthetic laser beam 12 by a transmission type reflection mirror 11. As the transmission type reflection mirror 11, a usual beam splitter can be used. The first laser beam 8 transmits the transmission type reflection mirror 11 just as it is, and the second laser beam 9 is all reflected by the transmission type reflection mirror 11. A first focus adjusting lens 13 is disposed between the short wavelength laser source 6 and the transmission type reflection mirror 11. Also, a second focus adjusting lens 14 is disposed between the long wave length laser source 7 and the transmission type reflection mirror 11.

The synthetic laser beam 12 is irradiated to the semiconductor device substrate 3 when a shutter 15 is opened. The synthetic laser beam 12 is not irradiated when the shutter 15 is closed.

The synthetic laser beam 12 is irradiated to the surface of the silicon film 5 in a direction orthogonal to the silicon film surface. The synthetic laser beam 12 is not always collected in an incident point or an incident area like a point P (hereinafter, to be referred to as an incident point). However, it is desirable that the synthetic laser beam 12 is collected to have an about tens-of-$\mu$m area. The degree of the beam collection can be adjusted by moving the first focus adjusting lenses 13 and the second focus adjusting lenses 14.

The synthetic laser beam 12 is scattered or irregularly reflected at the incident point P to have a corn shape and is inputted to a plurality of optical fibers 17. An end of each of the plurality of optical fibers 17 is provided to surround the incident point P on a semi-spherical surface having the incident point P as a center position. The plurality of optical fibers form a bundle wave guide. The other ends of all the optical fibers 17 are connected with an optical transmission path 18. Thus, all the incident light beams which are inputted to optical fibers 17 is transferred to the light beam transmission path 18. The light beam transmission path 18 is connected with a photo-multiplier 19. That is, most of the light beams inputted to the optical fibers 17 is supplied to the photo-multiplier 19. It should be noted that the optical fibers 17 and optical transmission path 18 may be made as a unit.

A spectroscope 21 is disposed between the photo-multiplier 19 and the light beam transmission path 18. The spectroscope 21 can separate the first laser beam and second laser beam with different wavelengths spatially. For example, a prism can be used as the spectroscope 21. As the spectroscope 21, various spectroscopes such as a wavelength separating lattice and a resonance parallel plane board are well known and can be used in place of the prism. The photo-multiplier section 19 is composed of a first photo-multiplier 22 and a second photo-multiplier 23. The first laser beam and second laser beam are separated by the spectroscope 21 and are inputted to the first photo multiplier 22 and second photo-multiplier 23, respectively.

The first photo-multiplier 22 and second photo-multiplier 23 output a first voltage signal 24 and a second voltage signal 25 proportional to the quantities of light beams which are inputted to the first photo-multiplier 22 and second photo-multiplier 23, respectively. The first voltage signal 24 and the second voltage signal 25 are supplied to a CPU 26. The CPU 26 is provided with an arithmetic and logic operation circuit 27. A shutter drive mechanism 28 is disposed between the CPU 26 and the shutter 15.

The CPU 26 drives the X-Y drive mechanism 2 in accordance with a program inputted to the CPU 26. Also, the CPU 26 drives the shutter drive mechanism 28 once in correspondence to the driving operation of the X-Y drive mechanism 2 such that the shutter 15 is opened for a predetermined time.

Figure 2:
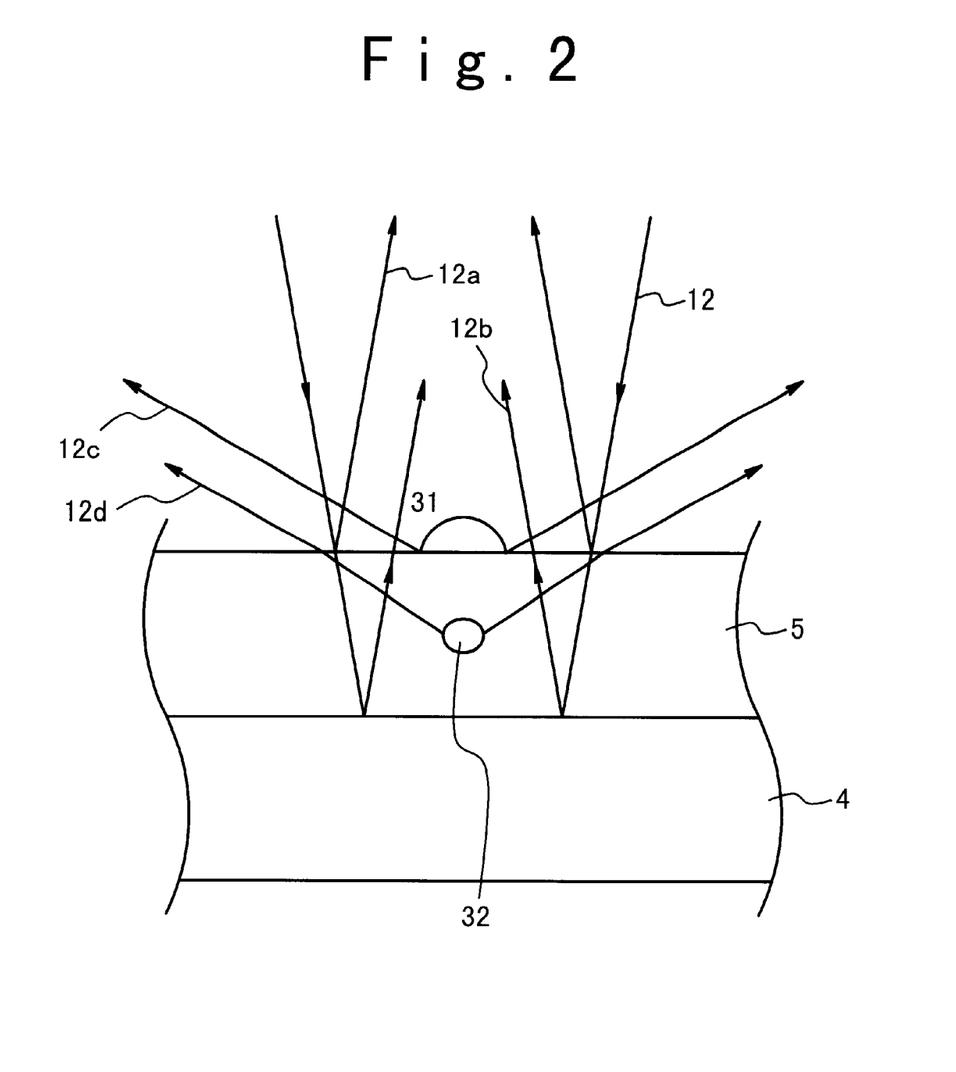
FIG. 2 is a diagram showing relation between light beams with different wavelengths and scattered light beams.

FIG. 2 is a diagram showing the state in which the synthetic laser beam 12 is irradiated to the silicon film 5 to be reflected regularly and irregularly, and then collected. This figure shows that a foreign substance fine particle 31 is adhered on the surface of the silicon film 5, and a hole 32 as another foreign substance particle is present in the silicon film 5.

The synthetic laser beam 12 is separated into a first regularly reflected light beam 12a, a second regularly reflected light beam 12b, a first irregularly reflected light beam 12c and a second irregularly reflected light beam 12d. The first regularly reflected light beam 12a is reflected on the first interface between air and the silicon oxide film 5. The second regularly reflected light beam 12b is refracted at the interface to be inputted to the silicon oxide film 5, reflected at a second interface between the silicon oxide film 5 and the substrate 4, and then refracted at the first interface again to be outputted into the air. The first irregularly reflected light beam 12c is irregularly reflected by the foreign substance file particle 31 and the second irregularly reflected light beam 12d is irregularly reflected by the hole 32.

It is supposed that the film thickness of the silicon film 5 is constant, and the light beam quantity 2Q of the synthetic laser pulse beam 12 is constant. In this case, the light quantity 2Q is a summation of the first laser light beam quantity and the second laser light beam quantity. Also, it is supposed that the first laser light beam quantity and the second laser light beam quantity are equal to each other.

The reflectivity K1 in the first interface for the first laser beam and the reflectivity K2 in the first interface for the second laser are different from each other. The reflected light beam quantity Q1 is Q1=K1Q, which is approximately constant, when the first laser beam is reflected in the first interface. The reflected light beam quantity Q2 is Q2=K2Q, which is approximately constant, when the second laser beam is reflected in the first interface. Thus, thee light beam quantity 12a of the first regularly reflected light beam and the light beam quantity 12c of the first irregularly reflected light beam are constant.

In the silicon film 5, the attenuation factor L1 of the first laser beam and the attenuation factor L2 of the second laser beam are different from each other. The light beam quantity Q3 when the first laser beam travels in the silicon film 5 and goes out from the silicon film 5 is approximately constant. That is, $$Q3=L1(Q-K1Q)=L1Q(1-K1)$$

Also, the light beam quantity Q4 when the second laser beam travels in the silicon film 5 and goes out from the silicon film 5 is approximately constant. That is, $$Q4=L2(Q-K2Q)=L2Q(1-K2)$$

The light beam quantity Q5 of the first laser beam which is irregularly scattered or reflected by a foreign substance fine particle 31 is represented by X1. Also, the light beam quantity Q6 of the second laser beam which is irregularly reflected by the foreign substance fine particle 31 is represented by X2. Also, the light beam quantity Q7 of the first laser beam which is irregularly reflected by a hole particle 32 is represented by Y1. Also, the light beam quantity Q8 of the second laser beam which is irregularly reflected by the hole particle 32 is represented by Y2. A variable attenuation factor in the silicon film 5 of the first laser beam is represented by V1. Also, a variable attenuation factor in the silicon film 5 of the second laser beam is represented by V2. In this case, the light beam quantity of the first laser beam which goes out of the silicon film 5 is V1Y1. Also, the light beam quantity of the second laser beam which goes out of the silicon film 5 is V2Y2.

Therefore, the light beam quantity Q1 of the first laser beam and the light beam quantity Q2 of the second laser beam which are measured by the first photo-multiplier 22 and second photo-multiplier 23 are obtained as follows.

$$Q1=K1Q+L1(Q-K1Q)+X1+V1Y1.$$

$$Q2=K2Q+L2(Q-K2Q)+X2+V2Y2.$$

In this case, the light beam quantity X1 and light beam quantity X2 satisfy X1=kX2 using a proportional constant k. Also, the light beam quantity Y1 and the light beam quantity Y2 satisfy Y1=sY2, using a proportional constant s. The variables in the simultaneous equations are only X and Y. Therefore, if measured values Q1 and Q2 are substituted for the simultaneous equations, the light beam quantity of the first laser beam and the light beam quantity of the second laser beam can be determined, when the first and second laser beams are reflected by the foreign substance fine particle 31 and the hole particle 32 and then inputted to the first photo-multiplier 22 and the second photo-multiplier 23.

The quantity V1Y1 and light beam quantity V2Y2 of the laser beams which are irregularly reflected by the hole particle 32 are different from each other. When a dimensionless quantity Z which is defined by the following equation is used, $$Z=\ln(V1Y1/V2Y2)=\ln(sV1/V2)$$

the values which are represented by the attenuation factors V1 and V2 correspond to the depth. Therefore, this dimensionless quantity Z is a data which shows the depth of the hole particle 32 in the silicon film 5. In this way, even if the foreign substance fine particle 31 and the hole particle 32 exist at the same time, the existence or non-existence of the foreign substance 31 on the silicon film 5 surface and the hole particle 32 in the silicon film 5 can be detected distinguishably by use of 2 wavelength laser beams. Also, the depth of the hole particle can be known.

Moreover, the grain diameter of the foreign substance 31 and that of the hole particle 32 can be determined from the reflected laser beam quantities X1 and Y1 which are determined through the above calculation. That is, the reflected laser beam quantity is calculated by the light beam scattering theory based on the grain diameter. When 3 wavelength laser beams can be used even if the film thickness of the silicon film 5 is not constant, the simultaneous equations are composed of 3 equations. Thus, the film thickness data can be obtained, in addition to existence or non-existence of both of the hole particle 32 and the foreign substance particle 31 and those grain diameters.

The quantity of laser beam irregularly reflected on the silicon film 5 surface which is not a mirror surface increases when the reflectivity is large and the refract factor is large. When surface irregular reflection as noise is more than the irregular reflection quantity by the foreign substance, the detection precision decreases. In such a case, in order to make surface irregular reflection quantity little, use of a laser beam with a longer wavelength is desirable.

Figure 3:
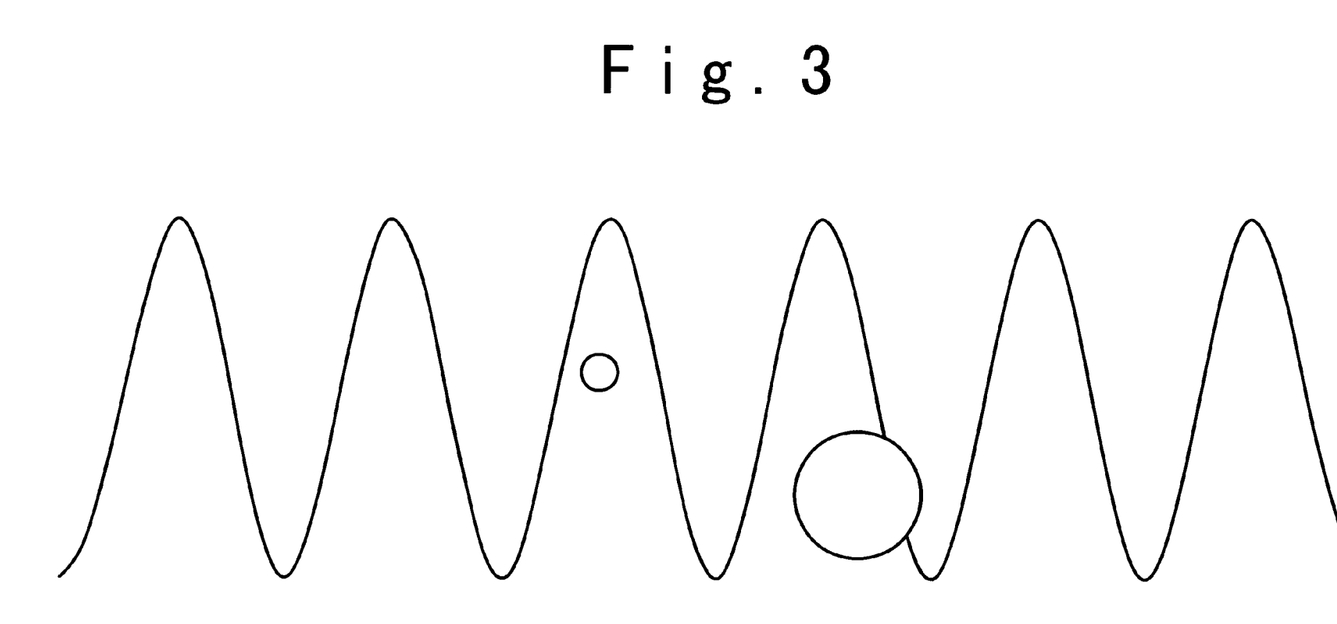
FIG. 3 is a diagram showing a light collecting section of the particle detecting apparatus according to a second embodiment of the present invention.

If an absorption quantity of the laser beam in the silicon film 5 increases by making the wavelength of the laser beam short, only the data near the silicon film 5 surface is obtained. Thus, the data in the direction of the depth can be removed. If the wavelength of the laser beam becomes long, the grain diameter of the particle to be possible to detect becomes large. Generally, it is possible to distinguishably detect existence of a particle, if the grain diameter is about a quarter of the wavelength, as shown in FIG. 3.

For this reason, it is desirable to use an Ar laser beam with the wavelength of 488 nm for the foreign substance with the gain diameter of 0.1 $\mu$m on the silicon film. If a N2 laser with the wavelength of 337 nm is used, it is possible to detect a foreign substance with the grain diameter equal to or less than 0.1 $\mu$m. By controlling an irregular reflection quantity by using the laser beams with various wavelength, the detection accuracy can be improved. The laser beam with the wavelength of 1.3 $\mu$m penetrates into Si.

A laser beam with the wavelength of 810 nm is absorbed up to the depth of about 5 $\mu$m. Also, a laser beam with the wavelength of 532 nm is absorbed up to the depth of about 0.5 $\mu$m. Therefore, it is necessary to use a laser beam with a longer wavelength to obtain information in the direction of the depth. However, it is difficult to detect a foreign substance with a small grain diameter when a laser beam with a longer wavelength is used.

By changing the wavelength of each of the 2 wavelength laser beams, the detection accuracy can be improved. That is, when the 2 wavelength laser beams are used, the information in the direction of the depth can be obtained. In addition, the detection precision can be improved. Also, when the information of a defect or hole in the silicon film 5 can be obtained when the laser beam with a longer wavelength is used.

By making the wavelength short to remove the information of the hole in the silicon film 5, only the foreign substance particle 31 on the film surface 5 can be detected, resulting in the improved detection accuracy of a surface foreign substance particle 31. In this way, when the wavelength of the first laser beam and the wavelength of the second laser beam are changed or controlled at the same time, the existence of the surface foreign substance particle and inner foreign substance particle and the detection of the grain diameters of particles can be improved.

Figure 4:
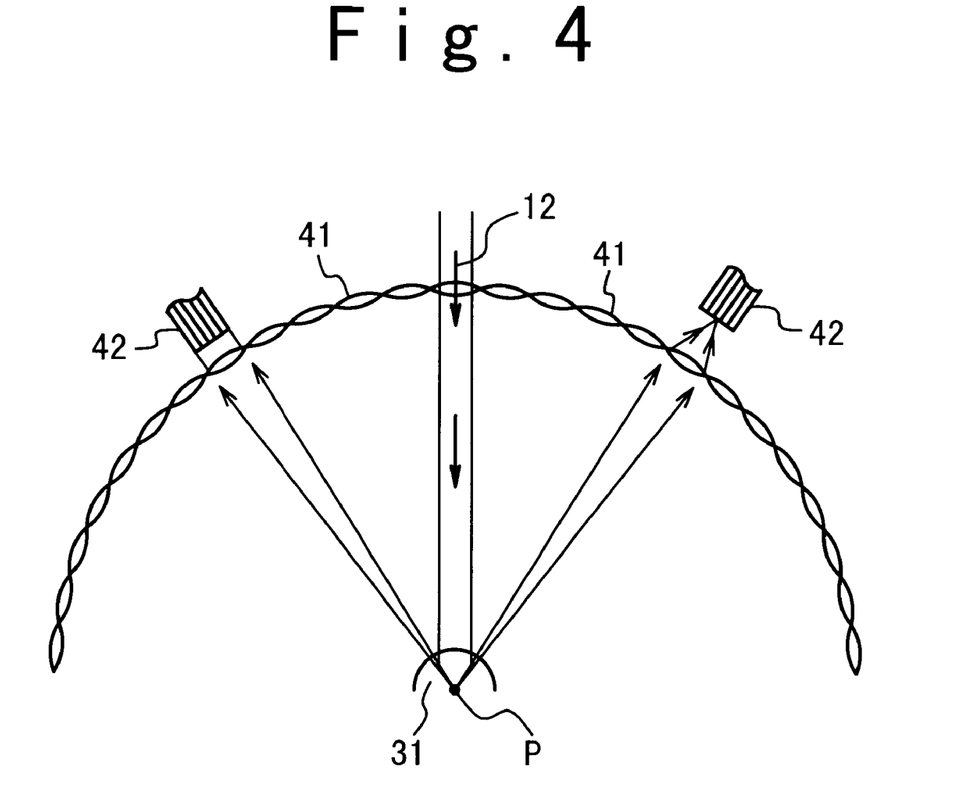
FIG. 4 is another light collecting section of the particle detecting apparatus according to a second embodiment of the present invention.

FIG. 4 shows the second embodiment of the reflected beam collecting section. The reflected beam collecting section shown in the figure is composed of a lot of small beam collecting lenses 41. Each of the lot of beam collecting lenses 41 is arranged on a semi-spherical surface centered on the incident point P of the synthetic laser beam 12. The light axis of each beam collecting lens 41 passes through the incident point P.

One optical fiber is provided for each beam collecting lens 41. A light wave guide bunch 42 is a set of one or more optical fibers. The centerline of an end of each optical fiber turns to pass through the incident point P. The method of directing the laser beams which are inputted to the beam collecting lenses 41 to the spectroscope section 21 is same as that described with reference to FIG. 1.

FIG. 4 shows 2 examples that the focal distances of the beam collecting lenses 41 are different. In one example, the irregular reflection light beam which passes the beam collecting lens 41 is collimated. In the other example, the irregular reflection light beam which passed the beam collecting lens 41 is collected for the optical fiber bundle 42.

The irradiation of the first laser beam and the second laser beam on the silicon film 5 may be performed separately. In this case, the shutter 15 is removed and, instead, two shutters (not illustrated) which operate independently are provided in the light beam path of the first laser beam 8 and the light beam path of the second laser beam 9. The two shutters are independently driven to be opened and closed by the shutter drive mechanism 28. In this case, the spectroscope section 21 is unnecessary and a single photo-multiplier 19 is only used. It is not necessary to say that the film thickness information can be obtained so that the detection precision can be improved, if 3 wavelength laser beams are used. It should be noted that accuracy of information of the film thickness and particle depth can be improved by selecting 2 or 3 wavelength laser beams from 3 or 4 wavelength laser beams or by sequentially selecting one of the 3 or 4 wavelength laser beams.

The measuring section for measuring a quantity of scattered light beam is composed of an photo-multiplier as a light beam quantity detecting section, a light transfer section for gathering and transferring the scattered light beam and a collecting section for collecting the scattered light beam. A combination of the lens for the collection and the optical fiber is illustrated as the collecting section. However, the lens for the collection is not always necessary. The collecting section may be composed of optical fibers, each of which has an end opening surface arranged on the semi-spherical surface to face the incident point P. Also, if the light beam receiving surface of the photo-multiplier is formed to have a semi-spherical shape so that the scattered light beams are directly received on the spherical surface, it is not necessary to use a light beam transmission path (optical fibers).

The detection precision of a foreign substance on the surface can be improved. For example, (1) it is possible to test a film formed wafer and to detect a foreign substance of 0.1 $\mu$m. The foreign substance of 0.1 nm can be detected by use of a laser beam with the wavelength shorter than 488 nm as one of the laser beams of 2 wavelengths. Also, (2) the irregular reflection quantity of the other wavelength laser beam as noise from the irregular surface becomes little because the wavelength of the other laser beam is long. Therefore, the noise can be removed from the difference between irregular reflection quantities with 2 wavelengths. Thus, the foreign substance particle on the film can be detected. It is possible to determine the data in the direction of the depth from the attenuation quantity of the scattered light beam by the film by use of the laser beams with 2 wavelengths. For instance, in case of the laser beam with the wavelength of 1.3 $\mu$m, the light beam passes through the silicon film, but the laser beams with the wavelength of 810 nm and 532 nm are absorbed up to the depth of about 5 $\mu$m and 0.5 $\mu$m. Thus, it is necessary to use a laser beam with a longer wavelength. The foreign substance particle with a small grain diameter can be detected by use of the laser beams of 2 wavelengths to inspect the foreign substance particle in the direction of the depth. Also, information in the direction of the depth can be removed such that the information of the hole particle in the silicon film can be removed, by making a wavelength short. That is, only the information of the film can be obtained, resulting in improvement of the foreign substance detection reliability.

What is claimed is:

1. A particle detecting apparatus for testing a substrate and a film provided on a top surface of said substrate, comprising:
a light source section for emitting first and second light beams respectively having first and second wavelengths which are different from each other, wherein said first and second light beams are directed to said substrate at a same time and orthogonal to said top surface;
an optical system for directing said first and second light beams to an incident point on said substrate, wherein said first and second light beams are scattered by said top surface of said substrate to produce first and second scattered light beams;
a light quantity measuring section for measuring a quantity of said first scattered light beam and a quantity of said second scattered light beam, wherein said light quantity measuring section comprises:
a beam collecting section for collecting said first scattered light beam and said second scattered light beam, comprising a set of optical fibers, wherein a first end of each of said optical fibers is arranged on a semi-spherical surface having the incident point as a center and a second end is connected to a light wave guide for guiding said first scattered light beam and said second scattered light beam;
a spectroscope for separating said first scattered light beam and said second scattered light beam guided by said light wave guide;
a first measuring section for measuring said quantity of said first scattered light beam separated by said spectroscope; and
a second measuring section for measuring said quantity of said second scattered light beam separated by said spectroscope; and
an operation section for detecting a foreign particle located on said film and in said film, and determining a diameter of said foreign particle and a depth of said foreign particle, based on said first scattered light beam quantity and said second scattered light beam quantity measured by said light quantity measuring section and independent of incidence angles of said first and second light beams.

2. A particle detecting apparatus according to claim 1, wherein said beam collecting section and said light wave guide are made as a unit, and said light wave guide comprises said set of optical fibers.

3. A particle detecting apparatus according to claim 1, wherein said beam collecting section further includes:
a set of lenses, each of which is provided for one of said optical fibers in front of said first end.

4. A particle detecting apparatus according to claim 1, wherein a wavelength of said first light beam is smaller than a grain diameter of said foreign particle.

5. A particle detecting apparatus according to claim 1, wherein the wavelength of said first light beam is shorter than 488 nm.

6. A particle detecting apparatus according to claim 1, wherein a wavelength of said first light beam is smaller than that of said second light beam, and the wavelength of said second light beam is smaller than a grain diameter of said foreign particle.

7. A particle detecting apparatus according to claim 1, wherein said first light beam is irregularly scattered by said foreign particle on a surface of said film to create a first irregularly scattered light beam and said second light beam is irregularly scattered by said top surface of said substrate to create a second irregularly scattered light beam.

8. A particle detecting apparatus according to claim 1, wherein a thickness of said film varies,
wherein said light source section emits a third light beam having a third wavelength different from said wavelengths of said first and second light beams and directed to said substrate at a same time as said first and second light beams,
wherein said third light beam is scattered by said substrate to produce a third scattered light beam,
wherein said light quantity measuring section measures a quantity of said third scattered light beam,
wherein said operation section detects a foreign particle located on said film, a foreign particle located in said film, and determines a thickness of said film, a diameter of said foreign particle and a depth of said foreign particle.

9. A particle detecting apparatus for testing a substrate and a film provided on a top surface of said substrate, comprising:
a light source section for emitting first and second light beams respectively having first and second wavelengths which are different from each other, wherein said first and second light beams are alternately directed to said substrate and orthogonal to said top surface;
an optical system for directing said first and second light beams to an incident point on said substrate, wherein said first and second light beams are scattered by said top surface of said substrate to produce first and second scattered light beams;
a light quantity measuring section for measuring a quantity of said first scattered light beam and a quantity of said second scattered light beam, wherein said light quantity measuring section comprises:
a beam collecting section for collecting said first scattered light beam and said second scattered light beam, comprising a set of optical fibers, wherein a first end of each of said optical fibers is arranged on a semi-spherical surface having the incident point as a center and a second end is connected to a light wave guide for guiding said first scattered light beam and said second scattered light beam; and
a measuring section for measuring said quantity of said first scattered light beam and said quantity of said second scattered light beam by said light wave guide; and
an operation section for detecting a foreign particle located on said film and in said film, and determining a diameter of said foreign particle and a depth of said foreign particle, based on said first scattered light beam quantity and said second scattered light beam quantity measured by said light quantity measuring section and independent of incidence angles of said first and second light beams.

10. A particle detecting apparatus according to claim 9, wherein said beam collecting section further comprises:
a set of lenses, each of which is provided for one of said optical fibers in front of said first end.

11. A method for detecting a foreign particle located on and in a film formed on a top surface of a substrate, comprising:
emitting a first light beam having a first wavelength;
emitting a second light beam having a second wavelength which is different from the first wavelength, wherein said first and second light beams are directed to said substrate at a same time;

directing said first and second light beams to an incident point on said top surface of said substrate and orthogonal to said top surface;

scattering said first light beam and said second light beam by said substrate to create a first and second scattered light beam, respectively;

measuring a quantity of said first scattered light beam and a quantity of said second scattered light beam, wherein said measuring comprises:

collecting said first scattered light beam and said second scattered light beam into a set of optical fibers by lenses;

guiding said first scattered light beam and said second scattered light beam;

after guiding said first scattered light beam and said second scattered light beam, using a spectroscope to separate said first scattered light beam and said second scattered light beam; and measuring said quantity of said first scattered light beam separated and said quantity of said second scattered light beam separated; and detecting a foreign particle located on said film and in said film and determining a diameter of said foreign particle and a depth of said foreign particle based on said first scattered light beam quantity and said second scattered light beam quantity measured by said light quantity measuring section and independent of incidence angles of said first and second scattered light beams.

12. A method according to claim 11, wherein a wavelength of said first light beam is smaller than a grain diameter of said foreign particle.

13. A method according to claim 11, wherein the wavelength of said first light beam is shorter than 488 nm.

14. A method according to claim 11, wherein a wavelength of said first light beam is smaller than a grain diameter of said foreign particle, a wavelength of said second light beam is larger than the grain diameter of said foreign particle.

15. A method according to claim 11, wherein a wavelength of said first light beam is smaller than that of said second light beam, and the wavelength of said second light beam is smaller than a grain diameter of said foreign particle.

16. A method for detecting a foreign particle located on and in a film formed on a top surface of a substrate, comprising:

emitting a first light beam having a first wavelength;

emitting a second light beam having a second wavelength which is different from the first wavelength, wherein said first and second light beams are alternately directed to said substrate;

directing said first and second light beams to an incident point on said top surface of said substrate and orthogonal to said top surface;

scattering said first light beam and said second light beam by said substrate to create a first and second scattered light beam, respectively;

measuring a quantity of said first scattered light beam and a quantity of said second scattered light beam, wherein said measuring comprises:

collecting said first scattered light beam and said second scattered light beam into a set of optical fibers by lenses; and measuring said quantity of said first scattered light beam and said quantity of said second scattered light beam, and detecting a foreign particle located on said film and in said film and determining a diameter of said foreign particle and a depth of said foreign particle based on said first scattered light beam quantity and said second scattered light beam quantity measured by said light quantity measuring section and independent of incidence angles of said first and second light beams.

17. A particle detecting apparatus for testing a substrate and a film provided on a top surface of said substrate, comprising:

a light source section for emitting first and second light beams respectively having first and second wavelengths which are different from each other;

an optical system for directing said first and second light beams to an incident point on said substrate and orthogonal to said top surface, wherein said first and second light beams are scattered by said top surface of said substrate to produce first and second scattered light beams;

a light quantity measuring section for measuring a quantity of said first scattered light beam and a quantity of said second scattered light beam; and an operation section for detecting a foreign particle located on said film and in said film, and determining a diameter of said foreign particle and a depth of said foreign particle, based on said first scattered light beam quantity and said second scattered light beam quantity measured by said light quantity measuring section and independent of incidence angles of said first and second light beams.

18. A particle detecting apparatus according to claim 17, wherein said light quantity measuring section comprises:

a beam collecting section for collecting said first scattered light beam and said second scattered light beam, comprising a set of optical fibers, wherein a first end of each of said optical fibers is arranged on a semi-spherical surface having the incident point as a center and a second end is connected to a light wave guide for guiding said first scattered light beam and said second scattered light beam;

a spectroscope for separating said first scattered light beam and said second scattered light beam guided by said light wave guide;

a first measuring section for measuring said quantity of said first scattered light beam separated by said spectroscope; and a second measuring section for measuring said quantity of said second scattered light beam separated by said spectroscope.

19. A particle detecting apparatus according to claim 18, wherein said beam collecting section and said light wave guide are made as a unit.

20. A particle detecting apparatus according to claim 19, wherein said light wave guide comprises said set of optical fibers.

21. A particle detecting apparatus according to claim 17, wherein said foreign particle includes a void formed in said substrate.

22. A particle detecting apparatus according to claim 17, wherein said apparatus detects an existence of said foreign particle having a diameter of less than 0.1 $\mu$m.

23. A particle detecting apparatus according to claim 17, wherein said apparatus distinguishes between a foreign particle which includes a hole formed in said substrate and a foreign particle which comprises a substance other than a hole.

* * * * *